United States Patent
Hage et al.

(10) Patent No.: US 6,854,316 B2
(45) Date of Patent: Feb. 15, 2005

(54) DEVICE FOR MEASURING THE STATIC AND/OR DYNAMIC FRICTION COEFFICIENT OF AN ARTIFICIAL GRASS LAWN FOR SPORTS FIELDS

(75) Inventors: Edward Hage, KJ Helmond (NL); Geurt Bastiaan Slootweg, JK Enschede (NL); Marinus Hendrikus Olde Weghuis, AB Oldenzaal (NL)

(73) Assignee: Ten Cate Thiolon B.V., Re Nijverdal (NL)

( * ) Notice: Subject to any disclaimer, the term of this patent is extended or adjusted under 35 U.S.C. 154(b) by 0 days.

(21) Appl. No.: 10/466,317
(22) PCT Filed: Feb. 1, 2002
(86) PCT No.: PCT/NL02/00076
§ 371 (c)(1),
(2), (4) Date: Jan. 7, 2004
(87) PCT Pub. No.: WO02/063279
PCT Pub. Date: Aug. 15, 2002

(65) Prior Publication Data
US 2004/0149005 A1 Aug. 5, 2004

(30) Foreign Application Priority Data
Feb. 7, 2001 (NL) .............................................. 1017303

(51) Int. Cl.$^7$ .............................................. G01N 19/02
(52) U.S. Cl. ............................................................. 73/9
(58) Field of Search .................................................. 73/9

(56) References Cited

U.S. PATENT DOCUMENTS

| 4,098,111 | A | | 7/1978 | Hardmark et al. | 73/9 |
|---|---|---|---|---|---|
| 4,194,387 | A | * | 3/1980 | Hofbauer et al. | 73/9 |
| 4,315,426 | A | * | 2/1982 | Brandon | 73/9 |
| 4,722,218 | A | | 2/1988 | Strader | 73/9 |
| 5,259,236 | A | * | 11/1993 | English | 73/9 |
| 5,734,088 | A | * | 3/1998 | Gunderson | 73/9 |
| 6,463,784 | B2 | * | 10/2002 | Kashiwagi et al. | 73/9 |

FOREIGN PATENT DOCUMENTS

DE  4201124 A1  7/1993

* cited by examiner

Primary Examiner—Hezron Williams
Assistant Examiner—John Fitzgerald
(74) Attorney, Agent, or Firm—Jacobson Holman PLLC

(57) ABSTRACT

A device for measuring the static and/or dynamic friction coefficient of a surface, in particular a natural or artificial grass surface, in which the device includes a frame to which a first arm is pivotally connected with one side, which first arm is pivotally connected at its other side to a bar fitted with a body having a surface which can be placed into contact with the surface to be measured, wherein the bar is furthermore connected to an element for exerting thereon a torque which acts about the pivot point thereon, and wherein loading elements are furthermore present for exerting a force on the bar in the direction of the surface to be measured, wherein the bar is furthermore provided with an element for measuring forces occurring in the bar, which element is present at a point located between the pivot point with the first arm and the side which is capable of carrying said body.

7 Claims, 2 Drawing Sheets

Figure 1:
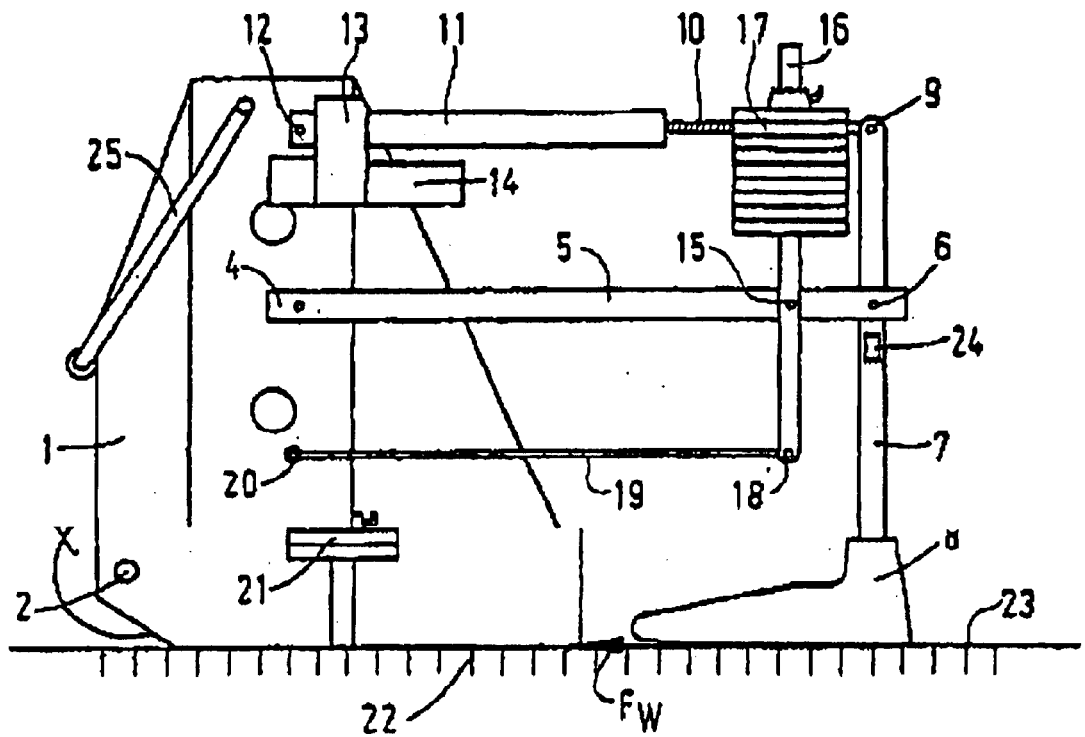

DEVICE FOR MEASURING THE STATIC AND/OR DYNAMIC FRICTION COEFFICIENT OF AN ARTIFICIAL GRASS LAWN FOR SPORTS FIELDS

This is a nationalization of PCT/NL02/00076, filed Feb. 1, 2002 and published in English.

The present invention relates to a device for measuring the static and/or dynamic friction coefficient of a surface, in particular a natural or artificial grass surface.

The use of artificial grass as a substitute for natural grass has received a lot of attention for a number of years already. Artificial grass lawns usually consist of fibres of various kinds of synthetic material, which are fixed to a mat of a carrier material by tufting or otherwise.

Having a knowledge of the properties and the behaviour of this kind of artificial grass is becoming more and more important, now that also applications such as soccer fields are being considered. In order to make fields of artificial grass in particular suitable for these applications as well, a number of relevant properties thereof need to be further improved. Especially the grip of the sports shoe on such a field and the sliding properties are to be considered in this connection. A safe artificial grass lawn should spare the player's feet optimally.

Several instruments and methods for measuring the sliding properties of fields of artificial grass and thus acquiring a greater insight into these properties have been proposed already. In practice it has become apparent, however, that the results and the ease of use of these instruments are not fully satisfactory.

The object of the present invention is to provide a device for measuring the static and/or dynamic friction coefficient of a surface which provides a reliable measuring result and which is furthermore user-friendly and easy to transport.

In order to accomplish that objective, the device according to the invention is characterized in that it comprises a frame to which a first arm is pivotally connected with one side, which first arm is pivotally connected at its other side to a bar fitted with a body that has a surface which can be placed into contact with the surface to be measured, wherein said bar is furthermore connected to means for exerting thereon a turning moment which acts about the pivot point thereon, and wherein loading means are furthermore present for exerting a force on the bar in the direction of the surface to be measured, wherein the bar is furthermore provided with means for measuring forces occurring in the bar, which means are present at a point located between the pivot point with the first arm and the side which is capable of carrying said body.

The means for measuring forces that occur in the bar may consist of strain gauges.

In this way, a relatively simple device is obtained, in which the body which is in contact with the surface to be measured can be in the form of an artificial foot, which can be fitted with various types of footwear in order to be able to measure the friction of these types of footwear with the artificial grass in question. The shoe rests on the artificial grass and a friction force will occur between the sole of the shoe and the artificial grass as a result of a turning moment being exerted about the pivot point with the first arm. By first measuring the turning moment that occurs in the bar in question upon standstill of the shoe with respect to the surface to be measured, which is done by means of the strain gauges, the static friction coefficient of the surface in question can be calculated therefrom. At one point, the turning moment that is being exerted will be larger than the frictional moment, and the shoe will start to move over the surface, and the force being exerted at that point can then be calculated by means of the strain gauges. In this way the dynamic friction coefficient is determined. It is possible to measure the rolling friction coefficient of the surface in question by attaching a rotatable roller to the bar instead of an artificial foot.

The means for exerting the aforesaid turning moment on the aforesaid bar may consist of a rod or spindle extending at least substantially parallel to the first arm, which rod or spindle is pivotally connected to a point on the bar on the one hand and pivotally connected to the frame on the other hand, and wherein furthermore means are present for varying the length of the rod or spindle between its two pivot points. The aforesaid rod or spindle may be a hydraulic or pneumatic rod or a screwed spindle, which mates with, respectively, a hydraulic or a pneumatic cylinder or a rotatable nut, which in turn is pivotally connected to the frame.

In this way, the first arm and the spindle or rod form a parallelogram construction together with the bar which carries the shoe that is in contact with the artificial grass surface and the pivot points on the frame, so that the position of the shoe with respect to the artificial grass surface to be measured will not change upon forward and backward movement of the shoe. A proper and continuous contact of the sole of the shoe with the surface in question is thus ensured.

In order to ensure a correct measurement of the friction coefficient of the artificial grass surface, the shoe, that is, the body that is connected to the aforesaid bar, must be pressed against the surface with a specific force. In order to realise this, loading means are present, which, according to an advantageous embodiment of the device according to the invention, may consist of an electromagnetic actuator whose movable anchor is connected to a point on the aforesaid first arm via an extension spring. In order to be able to vary the force with which the aforesaid body is pressed against the surface, and also in order to be able to compensate for any up-and-down movement of the first arm, force measuring means are mounted on the first arm, whose measuring value is fed to a control device, by means of which the force that is exerted by the actuator can be controlled. In this way it is possible either to maintain the force being exerted on the first arm by the actuator at a constant level or, under certain circumstances and if desired, to adapt interconnected by means of an axle 2, on both ends of which a wheel 3 is mounted. An arm 5 is pivotally connected to the mounting plates 1 about a point 4, which arm is connected to a bar 7 at its other side via a pivot point 6 and which carries a body 8 in the form of an artificial foot at its bottom side. At its upper side, the bar 7 is connected, via pivot point 9, to a spindle 10 which is accommodated in a nut 11 which is likewise pivotally connected to the mounting plates 1 via pivot point 10, and which can be rotated by means of an electric motor 14 via a transmission 13. It is also possible to move the bar 7 by means of a rotary motor mounted in the pivot point 6.

The arm 5 is pivotally connected, via pivot point 15, to a rod 16, on which loading weighs 17 can be placed.

At its bottom side, the rod 16 is connected to a rod 19 via pivot point 18, which rod in turn is connected to the mounting plates 1 via pivot point 20. Disposed within the space defined by the mounting plates 1 is furthermore a device for storing weights 21 that are not being used.

The operation of this device is as follows. The mounting plates 1 are placed with their underside 22, which may be fitted with adjusting feet, on the surface 23 whose friction coefficient is to be measured. The wheels 3 thus become detached from said surface and the shoe 8 will come into contact with the surface 23 with its underside. Then a force is exerted on the pivot point 9 of the bar 7 by means of electric motor 14, the nut 11 and the spindle 10.

As a result of this force, a turning moment will develop about the point 6, as a result of which the shoe 8 will be pulled to the rear, which movement is opposed by the friction force $F_w$ between the underside of the shoe 8 and the surface 23, however. This force $F_w$ sets up a bending moment in the bar 7, which bending moment is measured by means of a strain gauge 24. The bending force measured by the strain gauge 24 provides a measure for the friction force $F_w$, from which the friction coefficient of the surface 23 can be determined. The shoe 8 needs to be pressed against the surface 23 with a specific normal force, of course, which normal force is obtained by loading the arm 5 with loading weights 17 arranged on a bar 16 that pivots about the point 15. In order to prevent the centre of gravity of the weights 17 shifting with respect to the arm 5 upon lifting of the arm 5, the arm 16 is connected to the pivot point 20 via a pivot point 18 and a rod 19, so that a parallelogram is obtained, and when the arm 5 moves upwards, the weight 17 will move in such a manner that the centre of gravity of these weights will remain located on the same vertical line. In this way a measuring device is obtained by means of which the friction of artificial grass surfaces can be measured very adequately.

In to measure the static friction coefficient, in which the shoe is stationary, therefore, the electric motor 14 is controlled in such a manner that the force on pivot point 9 increases with time, during which the values measured by the strain gauges 24 are recorded. The force increases until a movement of about 5–10 degrees about pivot point 6 has been made. In to measure the dynamic friction coefficient, the electric motor 14 is controlled in such a manner that the pivot point 9 makes a predetermined movement at a constant speed, whereby the value measured by the strain gauges 24 is recorded. The point 9 thereby moves along a distance which corresponds to an angular distortion of bar 7 of 0°–45°, so that the fiction is measured with each of these inclined positions. The measurement is stopped when an angle of 45° is reached.

The bar 7 carrying the shoe 8 is mounted in the device in such a manner that its position can be changed, so that also the fiction that are occurs when a shoe points to the rear with its nose can be measured, also in inclined positions of the shoe 8. The device is positioned very firmly and stable on the surface 23, resting on one side of the mounting plates 1. Weights which are currently not used for loading the arm 5 can be stored temporarily in the device 21. The device furthermore comprises a handle 25, which is placed in the position of rest in FIG. 1 and which has been moved to an active position in FIGS. 2*a* and 2*b*, in which position this handle can be gripped in order to tilt the device so that it will come to rest on the wheels 3 and can be readily moved across the terrain. As is furthermore shown in FIGS. 2*a* and 2*b*, the whole is disconnected in the transport position in such a manner that the external dimensions will be minimal, so that device is easy to transport. The weights 17 are all stared in the device 21 in this position, and the spindle 10 is disconnected from the bar 7, so that the whole can be folded down, as a result of which the external dimensions will be very small.

Figure 2A:
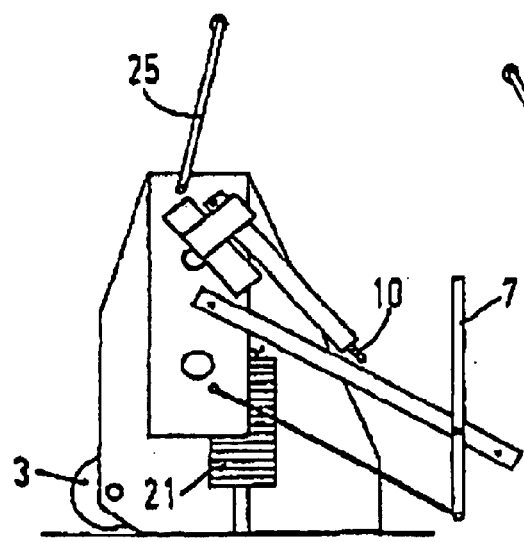
Figure 2B:
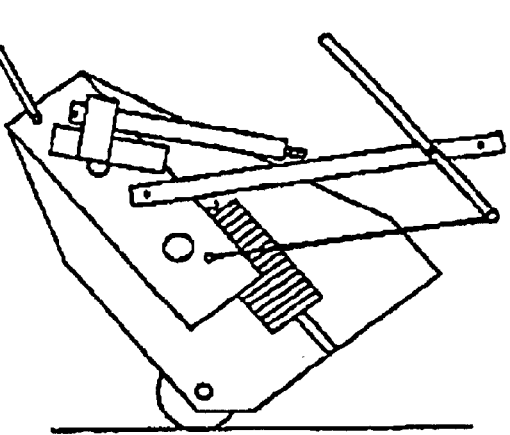
Figure 3:
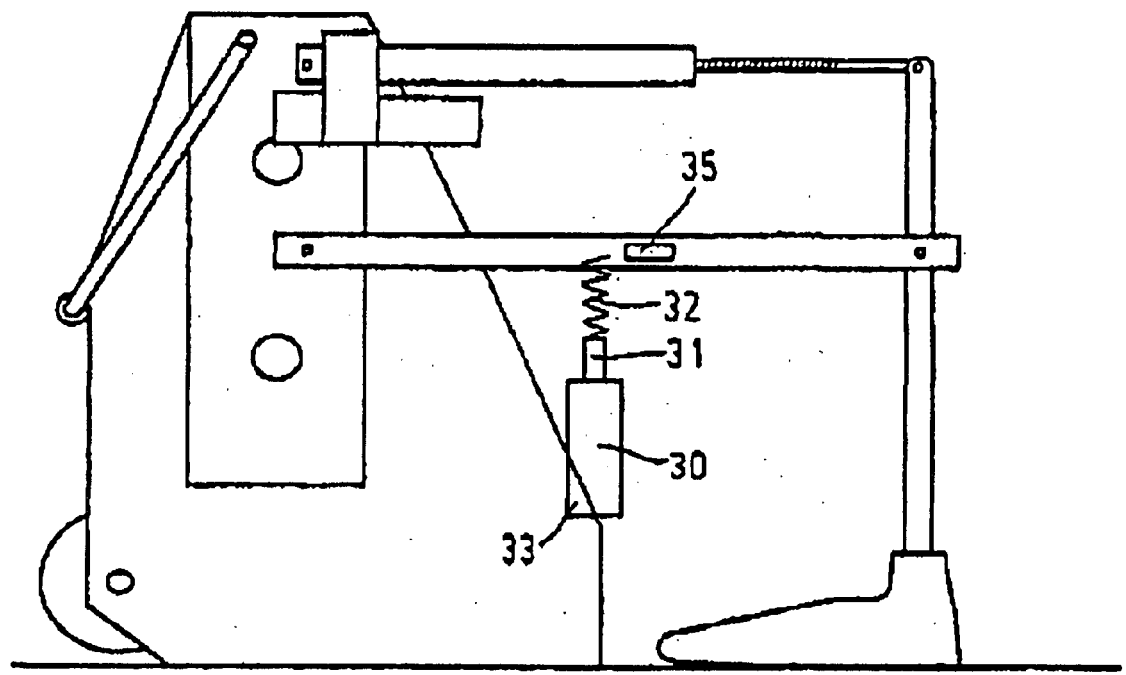

FIG. 3 schematically shows the device of FIG. 1, with this difference that the means of for loading the arm 5 are now in the form of an electromagnetic actuator 30, whose anchor 31 is coupled to the arm 5 via an extension spring 32. The actuator 30 itself is connected to the mounting plates 1 via pivot point 33. The force which is exerted on the arm 5 by the actuator 30 can be measured by means of a strain gauge 35, whose data can be fed to a control device (not shown), so that the load that is exerted on the arm 5 can be varied by means of this control device. This makes it possible to keep the load on the arm 5 constant even when the arm 5 is being moved upwards.

As has been said in the foregoing, it is possible to replace the artificial foot 8 by a rotatable roller for determining the roll friction of the surface 23, wherein the forces that occur in the bar 7 can be measured by means of the strain gauges 24 in the same manner as before.

What is claimed is:

1. A device for measuring the static and/or dynamic friction coefficient of a surface, said device comprising a frame, a first arm having a first arm end and a second arm end, said first arm being pivotally connected around a first pivot point with said first arm end to said frame and around a second pivot point with said second arm end to a first having a first bar end and a second bar end, said first bar being fitted at said first bar end with a body that has a surface placeable into contact with the surface to be measured, loading means for exerting a force on said first bar in a direction of the surface to be measured, the first bar being provided with means for measuring forces occurring in the first bar, which means are present at a point located between the second pivot point with the first arm and the first bar end, the first bar end being capable of carrying said body, said bar being connected with said second bar end around a third pivot point to means for exerting thereon a torque, which torque acts about the third pivot point thereon, thereby displacing said body relative to said frame.

2. The device according to claim 1, wherein the means for measuring the forces that occur in the first bar consist of strain gauges.

3. The device according to claim 1, wherein the loading means are formed by a second bar which is pivotally connected around a fifth pivot point to the first arm, and on said second bar weights are provided and which forms part of a square linkage in the form of a parallelogram.

4. The device according to claim 1, wherein the means for exerting the aforesaid torque on the first bar consist of a rod or spindle having a first rod end and a second rod end extending at least substantially parallel to the first arm, the rod or spindle is pivotally connected with a second rod end around said third pivot point to said second bar end and pivotally connected around a fourth pivot point with its first rod end to the frame, and wherein furthermore means are present for varying the length of the rod or spindle between said third and fourth pivot points.

5. The device according to claim 4, wherein said rod or spindle is a hydraulic or pneumatic rod or a screwed spindle, which mates with, respectively, a hydraulic or a pneumatic cylinder or a rotatable nut, wherein the cylinder or the nut is pivotally connected around the fourth pivot point to the frame.

6. The device according to claim 1, wherein the loading means consist of an electromagnetic actuator whose movable anchor is connected to a point on the first arm via an extension spring.

7. The device according to claim 6, wherein force measuring means are present on the first arm for controlling the force that is exerted by the actuator.

* * * * *